(12) United States Patent
Koehler et al.

(10) Patent No.: US 6,814,859 B2
(45) Date of Patent: Nov. 9, 2004

(54) FRIT MATERIAL AND BONDING METHOD FOR MICROFLUIDIC SEPARATION DEVICES

(75) Inventors: Jeffrey A. Koehler, Pasadena, CA (US); Paren P. Patel, Sierra Madre, CA (US)

(73) Assignee: Nanostream, Inc., Pasadena, CA (US)

( * ) Notice: Subject to any disclaimer, the term of this patent is extended or adjusted under 35 U.S.C. 154(b) by 0 days.

(21) Appl. No.: 10/256,505

(22) Filed: Sep. 27, 2002

(65) Prior Publication Data

US 2003/0150792 A1 Aug. 14, 2003

Related U.S. Application Data

(60) Provisional application No. 60/357,683, filed on Feb. 13, 2002, and provisional application No. 60/393,953, filed on Jul. 2, 2002.

(51) Int. Cl.[7] ............................................. B01D 15/08
(52) U.S. Cl. ...................... 210/198.2; 210/656; 422/70; 422/100; 73/61.52
(58) Field of Search .............................. 210/656, 198.2; 422/70, 100; 96/101; 73/61.52

(56) References Cited

U.S. PATENT DOCUMENTS

| 4,558,333 | A | 12/1985 | Sugitani et al. | 346/140 R |
|---|---|---|---|---|
| 5,039,493 | A | 8/1991 | Oprandy | 422/101 |
| 5,041,181 | A | 8/1991 | Brackett et al. | 156/84 |
| 5,070,606 | A | 12/1991 | Hoopman et al. | 29/890.03 |
| 5,376,252 | A | 12/1994 | Ekström et al. | |
| 5,443,890 | A | 8/1995 | Öhman | 428/167 |

(List continued on next page.)

FOREIGN PATENT DOCUMENTS

| EP | 0 708 331 A1 | 4/1996 |
|---|---|---|
| EP | 1 106 244 A2 | 6/2001 |
| WO | WO 97/06468 | 2/1997 |
| WO | WO 98/07069 | 2/1998 |
| WO | WO 98/45693 | 10/1998 |
| WO | WO 99/09042 | 2/1999 |

(List continued on next page.)

OTHER PUBLICATIONS

Olsen, Kimberly G. et al., *Immobilization of DNA Hydrogel Plugs in Microfluidic Channels*, "Analytical Chemistry," vol. 74, No. 6, Mar. 15, 2002, pp. 1436–1441.

Kameoka, Jun et al., *A Polymeric Microfluidic Chip for CE/MS Determination of Small Molecules*, "Analytical Chemistry," vol. 73, No. 9, May 1, 2001, pp. 1935–1941.

Fan, Z.H. et al., "Plastic Microfluidic Devices for DNA Sequencing and Protein Separations," *Micro Total Analysis Systems*, 2001, J.M. Ramsey and A. van den Berg (eds.), Kluwer Academic Publishers, the Netherlands, pp. 19–21.

Liu, Yingjie et al., "Microfabricated Polycarbonate CE Devices for DNA Analysis," *Micro Total Analysis Systems*, 2001, J.M. Ramsey and A. van den Berg (eds.), Kluwer Academic Publishers, the Netherlands, pp. 119–120.

(List continued on next page.)

*Primary Examiner*—Ernest G. Therkorn
(74) *Attorney, Agent, or Firm*—Vincent K. Gustafson; Michael F. Labbee (57) ABSTRACT

A frit for use in multi-layer microfluidic separation devices is provided. The frit comprises a polymeric membrane that may be securely bonded within the device and minimizes lateral wicking. A secure bond is ensured by treating the polymer to match its surface energy to that of the materials to which it is bound. Treatments include plasma treatment, irradiation and the application of acids.

23 Claims, 4 Drawing Sheets

U.S. PATENT DOCUMENTS

| | | | |
|---|---|---|---|
| 5,478,751 A | 12/1995 | Oosta et al. | 436/165 |
| 5,525,405 A | 6/1996 | Coverdell et al. | 428/213 |
| 5,690,763 A | 11/1997 | Ashmead et al. | 156/60 |
| 5,792,943 A * | 8/1998 | Craig | 210/198.2 |
| 5,846,396 A | 12/1998 | Zanzucchi et al. | 204/601 |
| 5,882,465 A | 3/1999 | McReynolds | 156/285 |
| 5,885,470 A | 3/1999 | Parce et al. | 216/33 |
| 5,922,210 A | 7/1999 | Brody et al. | 210/767 |
| 5,922,591 A | 7/1999 | Anderson et al. | 435/287.2 |
| 5,935,401 A | 8/1999 | Amigo | 204/454 |
| 6,010,607 A | 1/2000 | Ramsey | 204/435 |
| 6,033,546 A | 3/2000 | Ramsey | 204/603 |
| 6,043,080 A | 3/2000 | Lipshutz et al. | 435/287.2 |
| 6,048,498 A | 4/2000 | Kennedy | 422/99 |
| 6,068,751 A | 5/2000 | Neukermans | 204/601 |
| 6,073,482 A | 6/2000 | Moles | 73/53.01 |
| 6,074,725 A | 6/2000 | Kennedy | 428/188 |
| 6,149,870 A | 11/2000 | Parce et al. | 422/100 |
| 6,150,180 A | 11/2000 | Parce et al. | 436/514 |
| 6,156,438 A | 12/2000 | Gumm et al. | 428/458 |
| 6,240,790 B1 | 6/2001 | Swedberg et al. | |
| 6,267,858 B1 * | 7/2001 | Parce et al. | 204/600 |
| 6,312,888 B1 | 11/2001 | Wong et al. | 435/4 |
| 6,352,577 B1 | 3/2002 | Martin et al. | 96/4 |
| 6,408,878 B2 * | 6/2002 | Unger et al. | 137/597 |
| 6,428,896 B1 | 8/2002 | Ramsey et al. | 428/428 |
| 6,494,614 B1 | 12/2002 | Bennett et al. | 366/336 |
| 6,514,399 B1 | 2/2003 | Parce et al. | 204/600 |
| 6,537,433 B1 * | 3/2003 | Bryning et al. | 204/450 |
| 6,537,506 B1 | 3/2003 | Schwalbe et al. | 422/130 |
| 6,581,441 B1 * | 6/2003 | Paul | 210/656 |
| 6,623,860 B2 | 9/2003 | Hu et al. | 428/411.1 |
| 2002/0094533 A1 | 7/2002 | Hess et al. | 435/6 |
| 2002/0189947 A1 | 12/2002 | Paul et al. | |
| 2002/0199094 A1 | 12/2002 | Strand et al. | 713/150 |
| 2003/0180711 A1 | 9/2003 | Turner et al. | 435/4 |

FOREIGN PATENT DOCUMENTS

| | | |
|---|---|---|
| WO | WO 99/19717 | 4/1999 |
| WO | WO 99/33559 | 7/1999 |
| WO | WO 99/56954 | 11/1999 |
| WO | WO 99/60397 | 11/1999 |
| WO | WO 00/21659 | 4/2000 |
| WO | WO 01/01025 A2 | 1/2001 |
| WO | WO 01/09598 A1 | 2/2001 |
| WO | WO 01/38865 A1 | 5/2001 |
| WO | WO 02/28532 A2 | 4/2002 |
| WO | WO 02/30486 | 4/2002 |

OTHER PUBLICATIONS

Palm, Anders et al., "Integrated Sample Preparation and MALDI MS on a disc," *Micro Total Analysis Systems*, 2001, J.M. Ramsey and A. van den Berg (eds.), Kluwer Academic Publishers, the Netherlands, pp. 216–218.

Svedberg, Malin et al., "Electrospray From A Plastic Chip," *Micro Total Analysis Systems*, 2001, J.M. Ramsey and A. van den Berg (eds.), Kluwer Academic Publishers, the Netherlands, pp. 335–336.

Prins, M.W.J. et al., *Multichannel structures made from micrometre–thick plastic foils*, "J. Micromech. Microeng.," 9, (1999), pp. 362–363.

Martin, P.M. et al., "Fabrication of plastic microfluidic components," Part of the SPIE Conference on Microfluidic Devices and Systems, Santa Clara, California, Sep. 1998, SPIE Vo. 3515.

Nieh, Jenn–Yeu et al., *Hot Plate Welding of Polypropylene. Part I: Crystallization Kinetics*, "Polymer Engineering and Science," Jul. 1998, vol. 38, No. 7.

Nieh, Jenn–Yeu et al., *Hot Plate Welding of Polypropylene. Part II: Process Simulation*, "Polymer Engineering and Science," Jul. 1998, vol. 38, No. 7.

Vela, Adam, "An Approach for the Thermal Bonding of Micro–Fluidic Devices," Undergraduate Report, Institute for Systems Research, UG 2001-8.

Grodzinski, Dr. Piotr, "Development of Plastic Microfluidic Devices for Sample Preparation," Presentation from BioMEMS 2000, Columbus, Ohio, Sep. 24, 2000.

Nguyentat, Thinh, "Diffusion Bonding—An Advanced Material Process for Aerospace Technology," Web document published at http://www.vacets.org/vtic97/ttnguyen.htm.

Jacobson, Stephen C. et al., *Integrated Microdevice for DNA Restriction Fragment Analysis*, "Analytical Chemistry," vol. 68, No. 5, Mar. 1, 1996, pp. 720–723.

Moles, Dr. Donald R., "Microanalytical Systems Development at YSI: A Non–Silicon Approach," Presentation from BioMEMS & Biomedical Nanotechnology World 2000 Conference, Sep. 23–26, 2000.

Metz, Stefan et al., *Polyimide–based microfluidic devices*, "LAB on a Chip," 2001, 1, 29–34.

Soper, Steven A. et al., *Polymetric Microelectromechanical Systems*, "Analytical Chemistry," Oct. 1, 2000, pp. 643 A–651 A.

Ulbricht, Mathias et al., *Surface modification of ultrafiltration membranes by low temperature plasma, II. Graft polymerization onto polyacrylonitrile and polysulfone*, "Journal of Membrane Science," 111, (1996), 193–215.

Koehler, Jeffrey A. et al., *Intermolecular Forces between a Protein and a Hydrophilic Modified Polysulfone Film with Relevance to Filtration*, "Langmuir," vol. 16, No. 26, 2000, pp. 10419–10427.

Kaeselev, Bozena et al., *Photoinduced grafting of ultrafiltration membranes: comparison of poly(ether sulfone) and poly(sulfone)*, "Journal of Membrane Science," 194, (2001), 245–261.

Ocvirk, Gregor et al., *High Performance Liquid Chromatography Partially Integrated onto a Silicon Chip*, "Analytical Methods and Instrumentation," vol. 2, No. 2, 74–82, (1995).

Buranda, Tione et al. *Biomolecular Recognition on Well-–Characterized Beads Packed in Microfluidic Channels*, "Analytical Chemistry," vol. 74, No. 5, Mar. 1, 2002, pp. 1149–1156.

Moore, Roger E., et al., *A Microscale Electrospray Interface Incorporating a Monolithic, Poly(styrene–divinylbenzene) Support for On–Line Liquid Chromatography/Tandem Mass Spectrometry Analysis of Peptides and Proteins*, "Analytical Chemistry," vol. 70, No. 23, Dec. 1, 1998.

Martin, Peter M., et al., "Laminated Ceramic Microfluidic Components for Microreactor Applications," Web document published at: www.pnl.gov/microats/aboutus/publications/microfabrication/laminceramic–rev.pdf.

* cited by examiner

FRIT MATERIAL AND BONDING METHOD FOR MICROFLUIDIC SEPARATION DEVICES

STATEMENT OF RELATED APPLICATION(S)

This application claims priority to U.S. Provisional Patent Application Ser. Nos. 60/393,953, filed Jul. 2, 2002 and 60/357,683, filed Feb. 13, 2002, both currently pending.

FIELD OF THE INVENTION

The present invention relates to frit materials for use in microfluidic devices.

BACKGROUND OF THE INVENTION

Chemical and biological separations are routinely performed in various industrial and academic settings to determine the presence and/or quantity of individual species in complex sample mixtures. There exist various techniques for performing such separations. One separation technique, liquid chromatography, encompasses a number of methods that are used for separating closely related components of mixtures. Liquid chromatography is a physical method of separation involving a sample (or sample extract) being dissolved in a mobile phase (which may be a gas, a liquid, or a supercritical fluid). While carrying the sample, the mobile phase is then forced (e.g., by gravity, by applying pressure, or by applying an electric field) through a separation 'column' containing an immobile, immiscible stationary phase. Liquid chromatography has many applications including separation, identification, purification, and quantification of compounds within various mixtures.

One category of conventional chromatography includes pressure-driven systems. These systems are operated by supplying a pressurized mobile phase (typically one or more liquid solvents pressurized with a pump) to a separation column. Typical columns have dimensions of several (e.g., 10, 15, 25) centimeters in length and between 3–5 millimeters in diameter, with capillary columns typically having internal diameters between 3–200 microns. The columns are packed with very small diameter (e.g., 5 or 10 micron) particles. It is important to minimize any voids in a packed column, since voids or other irregularities in a separation system can affect the quality of the results of the separation. Thus, most conventional separation columns include specially designed end fittings (typically having compressible ferrule regions) designed to hold packed stationary phase material in place and prevent irregular flow-through regions.

One important component of conventional chromatography columns is a fine porous filter, commonly referred to as a "frit," which retains the stationary phase material within the column as separations are performed. Frits for conventional high performance liquid chromatography (HPLC) columns are typically composed of either a metal, such as stainless steel or titanium, or a polymer, such as polyethylene (PE) or poly (ether ether ketone) (PEEK). The frit pore sizes are typically about two microns for five-micron stationary phase particles. The thickness of such frits typically is between about thirty mils (about 760 microns) and about seventy-five mils (about 2000 microns).

There has been a growing interest in the manufacture and use of microfluidic systems to perform chromatography. This is because, when conducted in microfluidic volumes, chromatography may be carried out using very small volumes of liquid that enhance safety and reduce disposal quantities. One difficulty in fabricating microfluidic devices having integral HPLC columns, however, has been including frits within such devices.

One method proposed for fabricating microfluidic separation devices is disclosed in commonly-assigned, co-pending patent application Ser. No. 60/357,683 (filed Feb. 13, 2002). A plurality of stacked device layers or sheets define microfluidic structures within the device that form the separation columns. The columns are defined in one or more of the device layers by cutting or otherwise removing portions of the device layer such that the remaining portions of the device layer form the lateral boundaries or "walls" of the microstructures. The microstructures are completed by sandwiching the device layer between substrates and/or other device layers to form the "floors" and "ceilings" of the microstructures. The use of multi-layer construction permits robust devices to be fabricated quickly and inexpensively compared to surface micromachining or material deposition techniques that are conventionally employed to produce microfluidic devices.

Figure 1A:
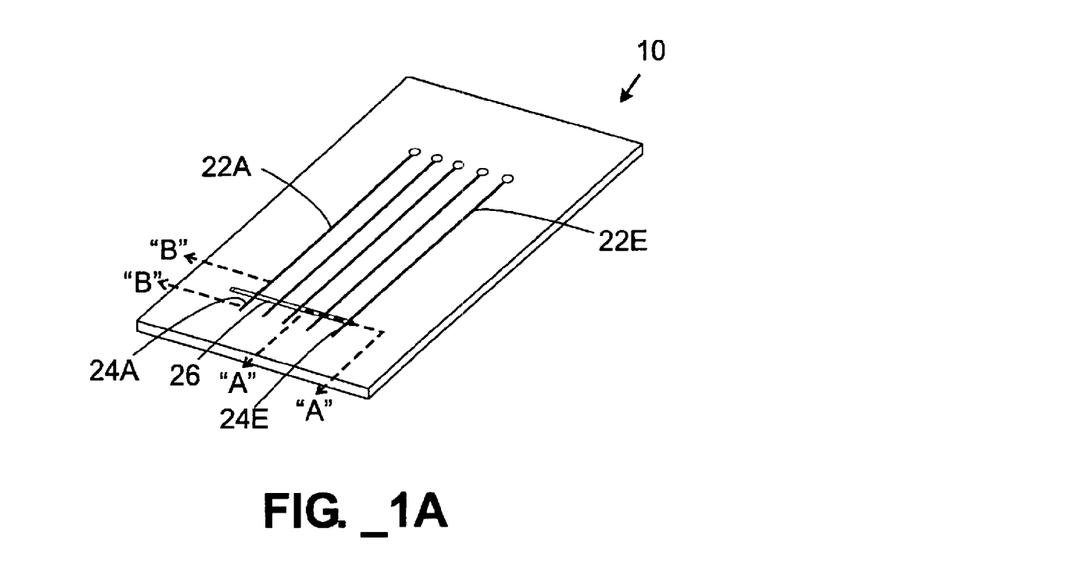
FIG. 1A is a perspective view of a multi-layer microfluidic separation device having five separation columns.
Figure 1B:
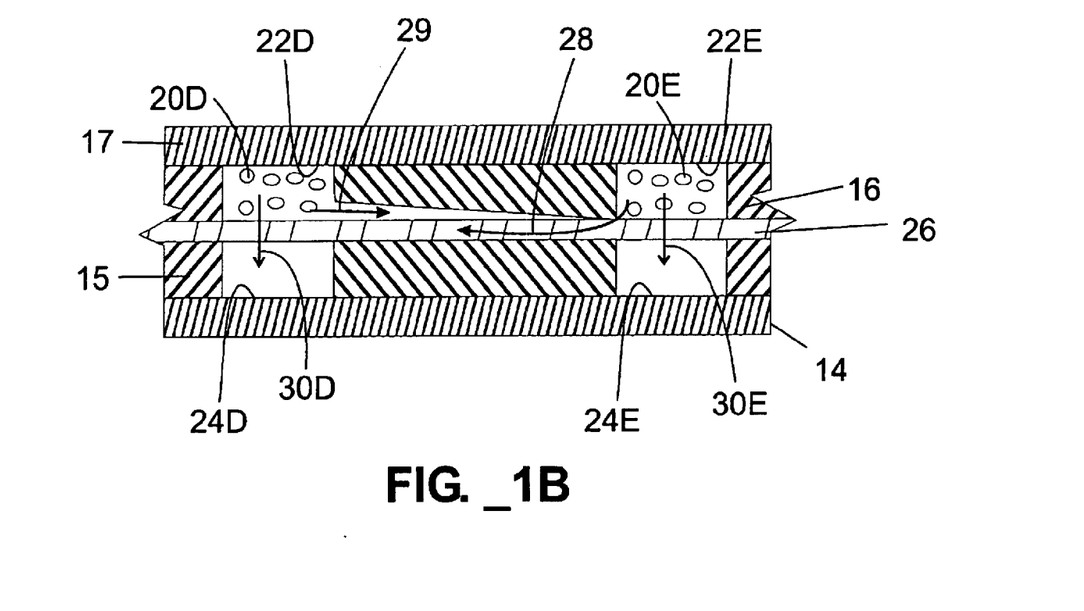
FIG. 1B is a partial cross sectional view of the device of FIG. 1A, taken along section line "A"—"A."
Figure 1C:
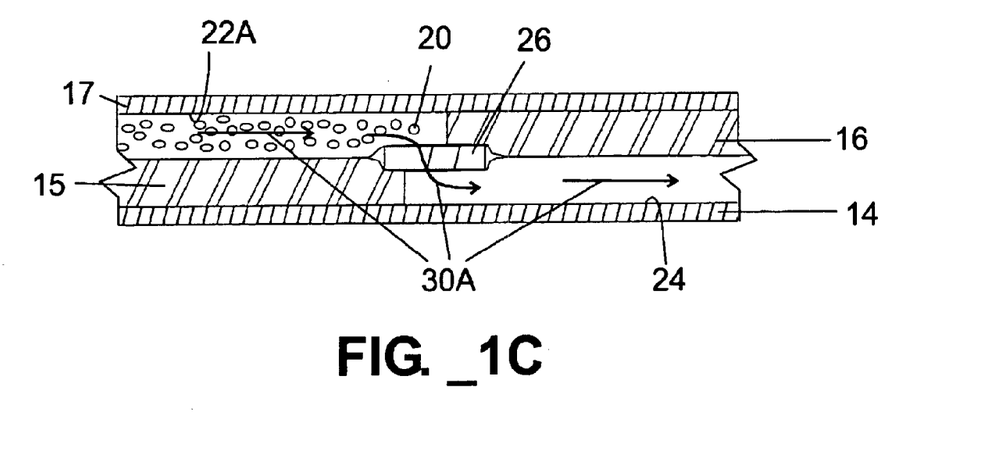
FIG. 1C is a partial cross sectional view of the device of FIG. 1A, taken along section line "B"—"B."

FIGS. 1A–1C show a simplified multi-layer microfluidic separation device 10 having a plurality of separation columns 22A–22E defined therein (with numbering for columns 22B–22D omitted for clarity). It will be readily understood by one skilled in the art that the device 10 illustrated in FIGS. 1A–1B has been simplified to illustrate the basic structure associated with multi-layer microfluidic separation devices and are not intended to limit the scope of the invention. Referring to FIG. 1C, the device 10 is fabricated with at least four device layers 14–17. The second device layer 16 defines the lateral boundaries of a plurality of separation columns 22A–22E. The third device layer 15 defines the lateral boundaries of a plurality of exit channels 24A–24E. The first and third device layers 14, 16 define the lower and upper boundaries, respectively, of the exit channels 24A–24E and the second and fourth device layers 15, 17 define the lower and upper boundaries, respectively, of the separation columns 22A–22E. A stationary phase material 20 is retained in the separation columns 22A–22E by a frit 26 positioned between the second and third device layers 15, 16. Thus, mobile phase solvent (as well as the sample compound being separated) flows through the system as indicated by arrows 30, while the stationary phase material 20 is kept in place by the frit 26.

Frit materials used with conventional chromatography columns have a thickness typically ranging from about thirty mils (760 microns) and about seventy-five mils (2000 microns). Because multi-layer multifluidic devices typically use device layer materials having thicknesses ranging from about one mil (twenty-five microns) to about twenty-five mils (635 microns), conventional HPLC frit materials are too thick to be used within a laminated multi-layer microfluidic separation device.

Moreover, certain conventional frit materials, such as stainless steel, may be difficult to bond to the polymer layers of a stacked layer device. In fact, conventional polymer frit materials also may be difficult to bond to other polymers, particularly where it is desirable to avoid the use of adhesives that could contaminate a microfluidic device. Adhesiveless bonding techniques may be used (e.g., by applying heat, pressure or a combination thereof) to attempt to bond a frit material directly to the surrounding device layers. However, it has been found that when frits are composed of material closely related to the material of the surrounding device layers, the temperature required to achieve the desired bonding tends to melt the frit to the degree that it is rendered inoperable or its effectiveness is reduced. When dissimilar materials are used, with desirable melting point differentials, device layer materials and frit materials bond less effectively, frequently resulting in undesirable separation of the layers from the frits at operational pressures.

Initial efforts to incorporate thin polymeric frit materials in multi-layer microfluidic separation devices included materials such as Nuclepore™, a track-etched polycarbonate membrane having a thickness of 6–11 microns, a pore size of 0.015–12.0 microns, and a pore density of $1 \times 10^5$–$6 \times 10^8$ pores/cm$^2$ (Whatman, Inc., Clifton, N.J.) (the "polycarbonate frit"). The polycarbonate frit presented several issues related to the fabrication and operation of the assembled device. First, the pore size of the polycarbonate frit is larger than the size of the stationary phase particulate material. Devices made with the polycarbonate frit suffered from a lack of reproducible pressure drop, which was believed to be caused by the clogging or blocking of the pores of the frit with the stationary phase material.

Figure 2:
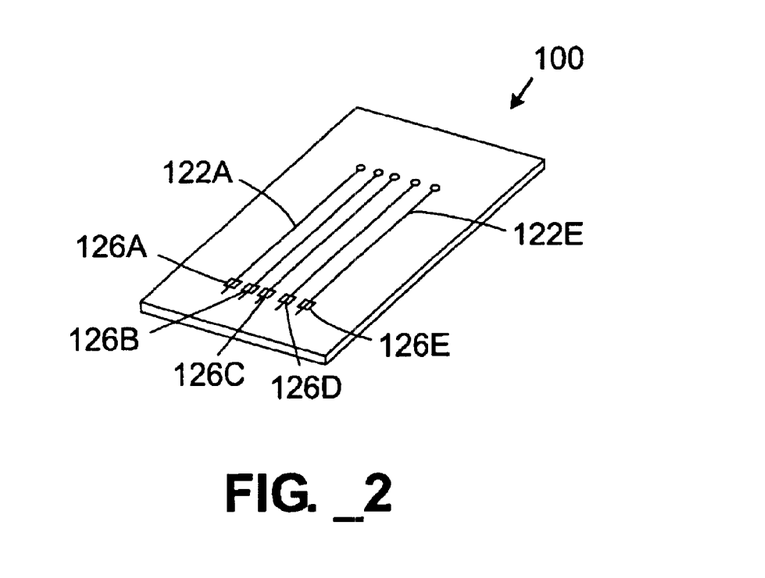
FIG. 2 is a perspective view of a multi-layer microfluidic separation device using individual frits for each separation column.

In addition, the polycarbonate frits have significantly different surface energy than the polymeric films most desirable for use in fabricating microfluidic separation devices (particularly polyolefins, including polypropylene). Also, the polycarbonate frits have at least one, if not two, very smooth surfaces. As a result, the bonding between the polycarbonate frit and the surrounding polymeric film was relatively weak, occasionally permitting undesirable fluid flow around the frit. For example, track-etched polycarbonate frits were selected to prevent wicking within the frit itself (such as that shown in FIG. 1B and indicated by flow arrow 28). However, because of the significantly different energies between the polycarbonate frit and the device layers and/or the smoothness of the polycarbonate frit, the bond therebetween was weak and allowed lateral wicking across the surface of the frit (such as that shown in FIG. 1B and indicated by flow arrow 29), thereby permitting cross contamination between separation columns 20D, 20E. Thus, to avoid wicking, as shown in FIG. 2, a device 100 using a polycarbonate frit would require multiple discrete frits 126A–126E, each placed in contact with one of the five separation channels 122A–122E, adding complexity and time to the assembly process for such devices.

Thus, it would be desirable to provide a frit material that is very thin, minimizes or eliminates wicking, and may be readily bonded to the device layers of a laminated multi-layer microfluidic device.

SUMMARY OF THE INVENTION

In one aspect of the present invention, a multi-layer microfluidic separation device comprises a first stencil layer that defines the lateral boundaries of a plurality of separation columns; a second stencil layer that defines the lateral boundaries of a plurality of exit channels; and a single frit having an upper surface and a lower surface. Each exit channel is in fluid communication with one of the separation columns, thereby forming a plurality of fluid flow paths. The upper surface of the frit is bonded to the first stencil layer. The lower surface of the frit is bonded to the second stencil layer. In this manner, the frit is disposed in the fluid flow paths. The frit permits flow in a direction substantially perpendicular to the upper surface and the lower surface. The upper surface of the frit is sufficiently bonded to the first stencil layer and the lower surface of the frit is sufficiently bonded to the second stencil layer to prevent substantially any lateral flow of fluid at an operating pressure either between the first stencil layer and the frit or between the second stencil layer and the frit.

In another aspect of the present invention, a method for fabricating a multi-layer microfluidic separation device comprises the steps of removing portions of a first device layer to define the lateral boundaries of a plurality of separation columns; removing portions a second device layer to define the lateral boundaries of a plurality of exit channels; providing a frit having an upper surface and a lower surface; and bonding the first device layer, the second device layer, and the frit such that each exit channel of the plurality of exit channels is in fluid communication with a separation column of the plurality of separation channels to form a plurality of fluid flow paths that flow through the frit. The frit is fabricated with a material that permits flow in a direction substantially perpendicular to the upper surface and the lower surface. The frit is pre-treated. The upper surface of the frit and the first stencil layer and the lower surface of the frit and the second stencil layer are sufficiently bonded to prevent substantially any unintended lateral flow of a fluid at an operating pressure either between the first stencil layer and the frit or between the second stencil layer and the frit.

DETAILED DESCRIPTION OF PREFERRED EMBODIMENTS OF THE INVENTION

Definitions

The terms "channel" or "chamber" as used herein are to be interpreted in a broad sense. Thus, they are not intended to be restricted to elongated configurations where the transverse or longitudinal dimension greatly exceeds the diameter or cross-sectional dimension. Rather, such terms are meant to comprise cavities or tunnels of any desired shape or configuration through which liquids may be directed. Such a fluid cavity may, for example, comprise a flow-through cell where fluid is to be continually passed or, alternatively, a chamber for holding a specified, discrete ratio of fluid for a specified ratio of time. "Channels" and "chambers" may be filled or may contain internal structures comprising, for example, valves, filters, and similar or equivalent components and materials.

The term 'frit' as used herein refers to a microporous material used to retain stationary phase material within a separation column for performing pressure-driven liquid chromatography.

The term "microfluidic" as used herein is to be understood to refer to structures or devices through which a fluid is capable of being passed or directed, wherein one or more of the dimensions is less than about five hundred microns or to fluidic volumes of less than or equal to about two microliters.

The terms "stencil" or "stencil layer" as used herein refers to a material layer or sheet that is preferably substantially planar, through which one or more variously shaped and oriented channels have been cut or otherwise removed through the entire thickness of the layer, thus permitting substantial fluid movement within the layer (as opposed to simple through-holes for transmitting fluid through one layer to another layer). The outlines of the cut or otherwise removed portions form the lateral boundaries of microstructures that are completed when a stencil is sandwiched between other layers, such as substrates and/or other stencils. Stencil layers can be either substantially rigid or flexible (thus permitting one or more layers to be manipulated so as not to lie in a plane).

Microfluidic Devices Generally

In an especially preferred embodiment, microfluidic devices according to the present invention are constructed using stencil layers or sheets to define channels and/or chambers. As noted previously, a stencil layer is preferably substantially planar and has a channel or chamber cut through the entire thickness of the layer to permit substantial fluid movement within that layer. Various means may be used to define such channels or chambers in stencil layers. For example, a computer-controlled plotter modified to accept a cutting blade may be used to cut various patterns through a material layer. Such a blade may be used either to cut sections to be detached and removed from the stencil layer, or to fashion slits that separate regions in the stencil layer without removing any material. Alternatively, a computer-controlled laser cutter may be used to cut portions through a material layer. While laser cutting may be used to yield precisely dimensioned microstructures, the use of a laser to cut a stencil layer inherently involves the removal of some material. Further examples of methods that may be employed to form stencil layers include conventional stamping or die-cutting technologies, including rotary cutters and other high throughput auto-aligning equipment (sometimes referred to as converters). The above-mentioned methods for cutting through a stencil layer or sheet permits robust devices to be fabricated quickly and inexpensively compared to conventional surface micromachining or material deposition techniques that are conventionally employed to produce microfluidic devices.

After a portion of a stencil layer is cut or removed, the outlines of the cut or otherwise removed portions form the lateral boundaries of microstructures that are completed upon sandwiching a stencil between substrates and/or other stencils. The thickness or height of the microstructures such as channels or chambers can be varied by altering the thickness of the stencil layer, or by using multiple substantially identical stencil layers stacked on top of one another. When assembled in a microfluidic device, the top and bottom surfaces of stencil layers are intended to mate with one or more adjacent layers (such as stencil layers or substrate layers) to form a substantially enclosed device, typically having at least one inlet port and at least one outlet port.

A wide variety of materials may be used to fabricate microfluidic devices having sandwiched stencil layers, including polymeric, metallic, and/or composite materials, to name a few. Various preferred embodiments utilize porous materials including filter materials. Substrates and stencils may be substantially rigid or flexible. Selection of particular materials for a desired application depends on numerous factors including: the types, concentrations, and residence times of substances (e.g., solvents, reactants, and products) present in regions of a device; temperature; pressure; pH; presence or absence of gases; and optical properties.

Various means may be used to seal or bond layers of a device together. For example, adhesives may be used. In one embodiment, one or more layers of a device may be fabricated from single- or double-sided adhesive tape, although other methods of adhering stencil layers may be used. Portions of the tape (of the desired shape and dimensions) can be cut and removed to form channels, chambers, and/or apertures. A tape stencil can then be placed on a supporting substrate with an appropriate cover layer, between layers of tape, or between layers of other materials. In one embodiment, stencil layers can be stacked on each other. In this embodiment, the thickness or height of the channels within a particular stencil layer can be varied by varying the thickness of the stencil layer (e.g., the tape carrier and the adhesive material thereon) or by using multiple substantially identical stencil layers stacked on top of one another. Various types of tape may be used with such an embodiment. Suitable tape carrier materials include but are not limited to polyesters, polycarbonates, polytetrafluoroethlyenes, polypropylenes, and polyimides. Such tapes may have various methods of curing, including curing by pressure, temperature, or chemical or optical interaction. The thickness of these carrier materials and adhesives may be varied.

In another embodiment, device layers may be directly bonded without using adhesives to provide high bond strength (which is especially desirable for high-pressure applications) and eliminate potential compatibility problems between such adhesives and solvents and/or samples. Specific examples of methods for directly bonding layers of non-biaxially-oriented polypropylene to form stencil-based microfluidic structures are disclosed in co-pending U.S. Provisional Patent Application Ser. Nos. 60/338,286 (filed Dec. 6, 2001) and 60/393,953 (filed Jul. 2, 2002), which are commonly owned by assignee of the present application and incorporated by reference as if fully set forth herein. In one embodiment, multiple layers of 7.5-mil (188 micron) thickness "Clear Tear Seal" polypropylene (American Profol, Cedar Rapids, Iowa) including at least one stencil layer may be stacked together, placed between glass platens and compressed to apply a pressure of 0.26 psi (1.79 kPa) to the layered stack, and then heated in an industrial oven for a period of approximately five hours at a temperature of 154° C. to yield a permanently bonded microstructure well-suited for use with high-pressure column packing methods. In another embodiment, multiple layers of 7.5-mil (188 micron) thickness "Clear Tear Seal" polypropylene (American Profol, Cedar Rapids, Iowa) including at least one stencil layer may be stacked together. Several microfluidic device assemblies may be stacked together, with a thin foil disposed between each device. The stack may then be placed between insulating platens, heated at 152° C. for about 5 hours, cooled with a forced flow of ambient air for at least about 30 minutes, heated again at 146° C. for about 15 hours, and then cooled in a manner identical to the first cooling step. During each heating step, a pressure of about 0.37 psi (2.55 kPa) is applied to the microfluidic devices.

Notably, stencil-based fabrication methods enable very rapid fabrication of devices, both for prototyping and for high-volume production. Rapid prototyping is invaluable for trying and optimizing new device designs, since designs may be quickly implemented, tested, and (if necessary) modified and further tested to achieve a desired result. The ability to prototype devices quickly with stencil fabrication methods also permits many different variants of a particular design to be tested and evaluated concurrently.

Further embodiments may be fabricated from various materials using well-known techniques such as embossing, stamping, molding, and soft lithography.

In addition to the use of adhesives and the adhesiveless bonding method discussed above, other techniques may be used to attach one or more of the various layers of microfluidic devices useful with the present invention, as would be recognized by one of ordinary skill in attaching materials. For example, attachment techniques including thermal, chemical, or light-activated bonding steps; mechanical attachment (such as using clamps or screws to apply pressure to the layers); and/or other equivalent coupling methods may be used.

Preferred Embodiments

Figure 3A:
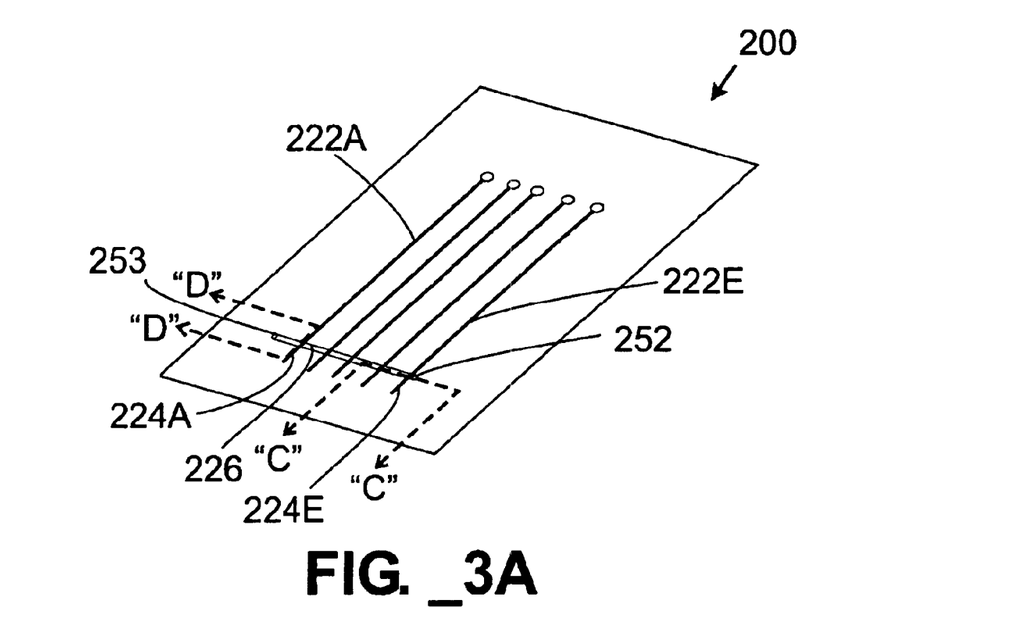
FIG. 3A is a perspective view of a multi-layer microfluidic separation device.
Figure 3B:
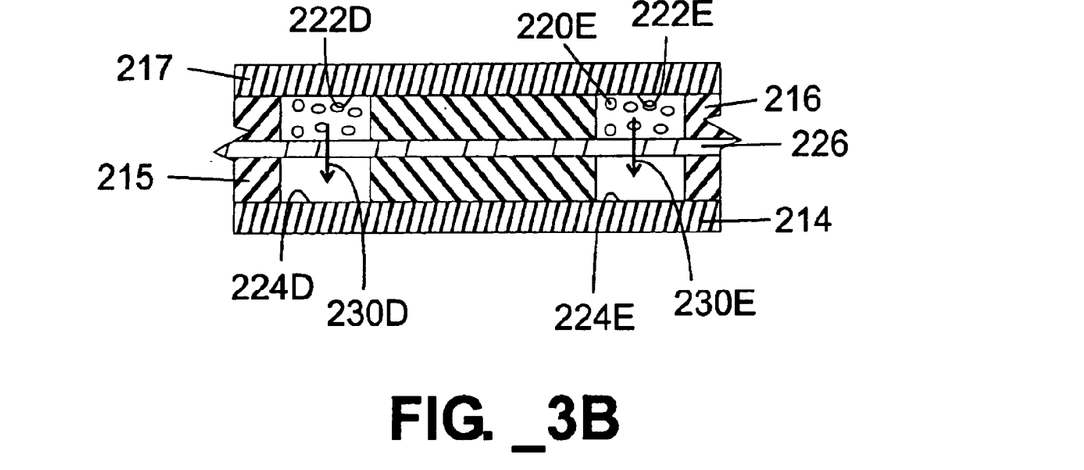
FIG. 3B is a partial cross sectional view of the device of FIG. 3A, taken along section line "C"—"C."
Figure 3C:
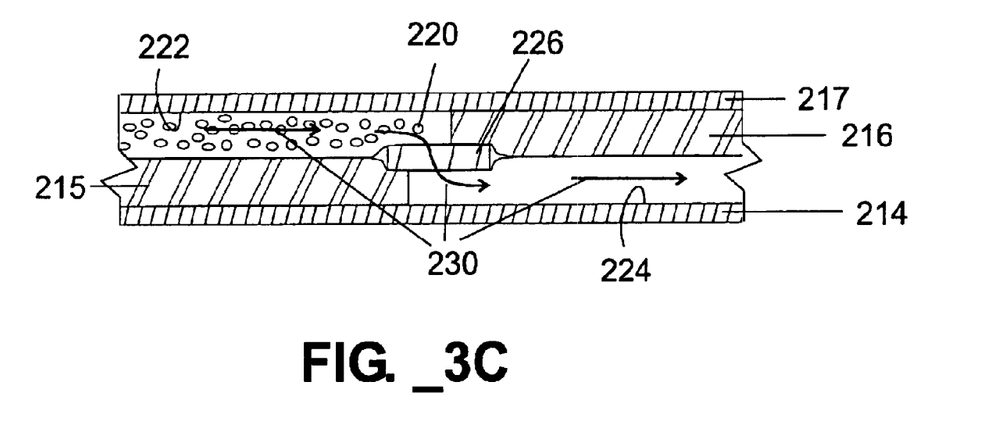
FIG. 3C is a partial cross sectional view of the device of FIG. 3A, taken along section line "D"—"D."

Applicants have demonstrated the bonding of a single strip of polypropylene frit material into a multi-column, microfluidic separation device composed of un-oriented polypropylene films, using one strip of frit material spanning multiple separation columns. FIGS. 3A-3C show a simplified version of a multi-layer microfluidic separation device 200 having a plurality of separation columns 222A–222E defined therein. It will be readily understood by one skilled in the art that the device 200 illustrated in FIGS. 3A-3B has been simplified to illustrate the basic structure associated with multi-layer microfluidic separation devices and is not intended to limit the invention. Other structures and arrangements will readily apparent to one skilled in the art. For example, multi-layer microfluidic separation devices according to the present invention may include any number of separation columns; other microfluidic structures, such as splitters, mixers, reaction chambers and other useful features; and/or multiple frits to retain stationary phase materials, act as a filter, prevent cross talk and other useful functions.

Referring to FIG. 3B, the device 200 is fabricated with multiple device layers 214–217, some of which are stencil layers 215, 216. A second device layer 216 defines the lateral boundaries of a plurality of separation columns 222A–222E and a third device layer 215 defines the lateral boundaries of a plurality of exit channels 224A–224E. The first and third device layers 214, 216, define the lower and upper boundaries, respectively, of the separation columns 222A–222E; and the second and fourth layers 215, 217, define the lower and upper boundaries, respectively, of the exit channels 224A–224E. A stationary phase material 220 is retained in the separation columns 222A–222E by a frit 226 positioned between the second device layer 216 and the third device layer 215. Thus, mobile phase solvent (as well as the sample compound being separated) flow through the system (as indicated by arrows 230) while the stationary phase material 220 is kept in place within the device 200.

The device layers 214–217 are fabricated with a substantially adhesiveless polyolefin material, such as non-biaxially-oriented polypropylene, using direct (e.g., thermal) bonding methods such as discussed herein. Stationary phase material 220 is preferably added to the device 200 after the various layers 214–217 and frit 226 are laminated (or otherwise bonded) together to form an integral structure. While various types of stationary phase material 220 may be used, preferred types include packed particulate material, and preferred packing methods employ slurry. One preferred slurry includes silica powder having surface chemical groups (e.g., Pinnacle II™ C-18 silica, 5-micron, catalog no. 551071, Restek Corp., Bellefonte, Pa.) and acetonitrile (MeCN), such as in a ratio of 1.00 grams particulate to 500 ml of solvent.

Although various materials may be used for the frit 226, a preferred material for fabricating the frit 26 is a permeable polypropylene membrane such as, for example, 1-mil (25 microns) thickness Celgard 2500 membrane (55% porosity, 0.209×0.054 micron pore size, Celgard Inc., Charlotte, N.C.). Preferably, the average pore size of the frit 26 is smaller than the average size of the particles of the particulate stationary phase material 220. More preferably, the average pore size of the frit 26 is at least one order of magnitude smaller than the average size of the particles of the particulate stationary phase material 220.

A polypropylene membrane frit material 26 is particularly preferred when the device layers 214–217 are fabricated with a substantially adhesiveless polyolefin material, such as non-biaxially-oriented polypropylene, using direct (e.g. thermal) bonding methods such as discussed herein. This material has two relatively rough surfaces, which may further enhance bonding with other materials. Devices 200 constructed according to such methods may be readily capable of withstanding (internal) operating pressures of 10 psi (69 kPa), 50 psi (345 kPa), 100 psi (690 kPa), 500 psi (3450 kPa), or even greater pressures.

It has been found that, for the bonding process to completely seal around a frit layer that is smaller than the dimensions of the microfluidic device, the frit layer must be less than about two mils (about 50 microns) thick, more preferably less than about one mil (about 25 microns) thick. For example, as shown in FIG. 3A, in one embodiment, the orientation of the frit material 226 is such that the strip is cut with the narrow dimension of the strip parallel to the machine direction of the frit material 226 so that the shrinkage of the frit material 226 will not affect the dimensions of the microfluidic device 200. In an alternate embodiment, the orientation of the frit material 226 is such that the strip is cut with the narrow dimension of the strip perpendicular to the machine direction of the frit material 226 and, during bonding, the ends of the frit material 226 may be tacked at its endpoints 252–253 to minimize shrinkage of the frit material 226, thus not affecting the dimensions of the microfluidic device 200. A representative microfluidic device is shown in commonly assigned, co-pending patent application Ser. No. 60/357,683 (filed Feb. 13, 2002).

The frit material was chosen such that its structure was similar to a mesh (which permits flow mainly in the direction perpendicular to the frit surface) as opposed to a depth filter (a polymer matrix that can allow tangential flow in the frit) in order to minimize or eliminate no cross-flow between channels across which a single strip of the frit material spans. For example, track-etched membranes and stretched polymer films (to induce micron sized pores) may be used to minimize lateral wicking.

In one embodiment in which high pressure (the specific pressure and time for bonding will depend upon the temperature and material selected) is applied to the polymer stack during bonding, the frit material can be chosen with a melting point temperature less than or equal to that of the polymer film. The bonding occurs at a temperature less than the melting point temperature of both the frit material and the polymer film due to interlayer flow induced at high pressures. Any portion of the polymer film material not under pressure (e.g., regions directly below voids such as channels, chambers or vias) will not melt or flow, leaving features and the pore structure of the frit material intact.

More preferably, a frit material is chosen such that its melting point temperature is significantly higher than that of the film material to which it bonds so that the polymer comprising the film can melt and flow into or through the frit material without melting the frit material (which would cause a loss of pore structure and, thus, loss of functionality). Minimal pressure may be applied during the bonding at a temperature that is above the melting point of the polymer film, but less than the melting point of the frit material.

Alternatively, hot press stamping can be used to bond the film layers immediately around the frit using a stamp that is designed (e.g., patterned with raised portions and/or recesses) to heat the entire frit area except for the locations on the layer that contain features (e.g., desirable microstructures such as channels, chambers, vias and the like). Preferably, the patterned stamp will be heated above the melting point of the polymer film. More preferably, the patterned stamp will be heated to a temperature above the melting points of both the film and the frit material. Pressure may be applied to the patterned stamp, such as by using either a mechanical or hydraulic press.

In another embodiment, multiple stacked layers of the microfluidic device are subjected to high pressure prior to bonding to reduce the diffusion length of the polymer to allow for shorter bonding times. For example, a mechanical or hydraulic press could be used. High pressure may be applied to substantially all of the device layers or just the layers immediately around the frit. While the specific pressure to be applied depends on the materials used, it is expected that polymers with high hardness values will require higher pressures than those with lower hardness values.

In one embodiment, a frit material is chosen such that the surface energy of the frit material is similar to the surface energy of the polymeric film to which it bonds. For a strong bond, a frit material is preferably chosen within the same general surface energy class as the polymer to which it must bond. The classes are generally classified as "low surface energy" polymers (approximately 18 to 36 dynes/cm) and "high surface energy" polymers (approximately 36 to 50 dynes/cm). More preferably, the surface energy differential between the frit material and the polymer film should be within about 5 dynes/cm for proper bonding, without regard to surface energy class. Even more preferably, the surface energy differential between the frit material and the polymer film should be within about 2 dynes/cm for proper bonding. Most preferably, the surface energy differential between the frit material and the polymer film should be within about 1 dyne/cm, or better yet about 0 dynes/cm, for the strongest bonding.

Of course, materials having desirable surface energy differentials may have undesirable melting point temperatures. In such an event, surface modification techniques may be used to alter the surface chemistry of the polymeric film and/or the frit material to improve the strength of the bond between the materials. It is believed that the applicable mechanism(s) include surface energy matching and/or surface roughening. Methods that can be used to modify the surfaces include low temperature plasma, ultraviolet light, or chemical activation of the surfaces.

A preferable method for plasma modification of surfaces is to initiate an oxygen plasma at about 175 mTorr (about 233.3 bar) with a 13.67 MHz, 25 W (25 joules) source for about one minute. A more preferable method of modification is to subsequently react the surface with an unsaturated organic molecule, such as hydroxyethyl methacrylate or vinyl pyrrolidone to alter the surface chemistry and, thus, surface energy. Other organic or inorganic molecules may be used.

A preferable method for ultraviolet light treatment of surfaces is to irradiate the surface at an irradiation energy of <100 mJ/cm2 using a 300 nm lamp in the presence of ozone. A more preferable method of modification is to subsequently react the surface with an unsaturated molecule, such as hydroxyethyl methacrylate or vinyl pyrrolidone to alter the surface chemistry and, thus, surface energy. Other organic or inorganic molecules may be used.

Organic chemical reactions may also be performed without a plasma or ultraviolet light activation step. A preferable method is to modify the surface using a strong acid, such as sulfuric acid. A more preferable method is to use a free radical initiator, such as azo(isobutyronitrile), along with an unsaturated molecule, such as hydroxyethyl methacrylate or vinyl pyrrolidone, and heat the solution to 80° C. to allow for incorporation of the unsaturated molecule into the polymer matrix.

Surface modification techniques may also be used to facilitate the flow of different solvents through the frit material by altering the hydrophobic/hydrophilic interaction balance as well as the polar/non-polar interaction balance. A preferable method is to physisorb a surfactant. For example, one may flow a surfactant solution into the completed device and allow it to interact with the surfaces before flushing the unadsorbed surfactant out of the chip, such as a polypropylene oxide/polyethylene oxide block polymer, in the pores of the frit material. An alternate method is to use ultraviolet light activation (as outlined previously). As a more preferable alternative, a plasma-induced modification could be performed on the surface (as outlined previously).

It is also to be appreciated that the foregoing description of the invention has been presented for purposes of illustration and explanation and is not intended to limit the invention to the precise manner of practice herein. It is to be appreciated therefore, that changes may be made by those skilled in the art without departing from the spirit of the invention and that the scope of the invention should be interpreted with respect to the following claims.

What is claimed is:

1. A multi-layer microfluidic separation device comprising:
    a first stencil layer defining the lateral boundaries of a plurality of separation columns;
    a second stencil layer defining the lateral boundaries of a plurality of exit channels wherein the plurality of exit channels is in fluid communication with the plurality of separation channels to form a plurality of fluid flow paths; and
    a single frit having an upper surface and a lower surface, wherein the upper surface is bonded to the first stencil layer and the lower surface is bonded to the second stencil layer such that the frit layer is disposed within at least two fluid flow paths of the plurality of fluid flow paths;
    wherein the frit permits flow in a direction substantially perpendicular to the upper surface and the lower surface;
    wherein the upper surface is sufficiently bonded to the first stencil layer and the lower surface is sufficiently bonded to the second stencil layer to prevent substantially any lateral flow of fluid at an operating pressure either between the first stencil layer and the frit or between the second stencil layer and the frit.

2. The multi-layer microfluidic separation device of claim 1 wherein the operating pressure is at least about 10 psi (69 kPa).

3. The multi-layer microfluidic separation device of claim 1 wherein the operating pressure is at least about 50 psi (345 kPa).

4. The multi-layer microfluidic separation device of claim 1 wherein the operating pressure is at least about 100 psi (690 kPa).

5. The multi-layer microfluidic separation device of claim 1 wherein the operating pressure is at least about 500 psi (3450 kPa).

6. The multi-layer microfluidic separation device of claim 1 wherein each separation column of the plurality of separation columns contains stationary phase material.

7. The multi-layer microfluidic separation device of claim 6 wherein the stationary phase material includes particulate material having an average particle size.

8. The multi-layer microfluidic separation device of claim 6 wherein the frit has an average pore size and the average pore size is smaller than the average particle size.

9. The multi-layer microfluidic separation device of claim 7 wherein the frit has an average pore size and the average pore size is no greater than about one-tenth of the average particle size.

10. The multi-layer microfluidic separation device of claim 1 wherein the frit comprises a permeable polypropylene membrane.

11. The multi-layer microfluidic separation device of claim 1 wherein the frit comprises a track-etched membrane.

12. The multi-layer microfluidic separation device of claim 1 wherein the frit comprises a stretched polymer film.

13. The multi-layer microfluidic separation device of claim 1 wherein the frit has a mesh structure.

14. The multi-layer microfluidic separation device of claim 1 wherein the frit is about 25 microns thick, is about 55% porous, and has a plurality of pores about 0.209×0.054 microns in size.

15. The multi-layer microfluidic separation device of claim 1 wherein:

the first stencil layer has a first surface energy;

the second stencil layer has a second surface energy;

the frit has a third surface energy; and the difference between any of the first surface energy, the second surface energy, and the third surface energy is less than or equal to about 5 dynes/cm.

16. The multi-layer microfluidic separation device of claim 15 wherein the difference between any of the first surface energy, the second surface energy, the third surface energy is less than or equal to about 2 dynes/cm.

17. The multi-layer microfluidic separation device of claim 15 wherein the difference between any of the first surface energy, the second surface energy, and the third surface energy is less than or equal to about 1 dynes/cm.

18. The multi-layer microfluidic separation device of claim 15 the difference between any of the first surface energy, the second surface energy, and the third surface energy is about 0 dynes/cm.

19. The multi-layer microfluidic separation device of claim 15 wherein the first surface energy, the second surface energy, and the third surface energy are substantially the same.

20. The multi-layer microfluidic separation device of claim 1 wherein any of the first stencil layer and the second stencil layer is a substantially adhesiveless polyolefin material.

21. The multi-layer microfluidic separation device of claim 20 wherein the substantially adhesiveless polyolefin material comprises unoriented polypropylene.

22. The multi-layer microfluidic separation device of claim 1 wherein the frit has a melting point temperature that is significantly higher than the melting point temperature of any of the first stencil layer and the second stencil layer.

23. The multi-layer microfluidic separation device of claim 1 wherein the frit comprises a surface treated polymer membrane.

* * * * *